United States Patent
Dong et al.

(10) Patent No.: US 7,114,850 B2
(45) Date of Patent: Oct. 3, 2006

(54) METHOD FOR TUBE SPIT CORRECTION BASED ON HIGH VOLTAGE OUTPUT

(75) Inventors: Fang F. Dong, Waukesha, WI (US); Jiang Hsieh, Brookfield, WI (US); Bruce M. Dunham, Mequon, WI (US); Clarence L. Gordon, III, Mequon, WI (US)

(73) Assignee: General Electric Company, Schenectady, NY (US)

( * ) Notice: Subject to any disclaimer, the term of this patent is extended or adjusted under 35 U.S.C. 154(b) by 312 days.

(21) Appl. No.: 10/604,956

(22) Filed: Aug. 28, 2003

(65) Prior Publication Data
US 2005/0047551 A1   Mar. 3, 2005

(51) Int. Cl.
*G01D 18/00* (2006.01)

(52) U.S. Cl. ........................ 378/207; 378/118
(58) Field of Classification Search ............ 378/4, 378/19, 101, 117, 118, 207, 901
See application file for complete search history.

(56) References Cited

U.S. PATENT DOCUMENTS 6,466,645 B1 * 10/2002 Hsieh et al. .............. 378/101

* cited by examiner

*Primary Examiner*—Edward J. Glick
*Assistant Examiner*—Courtney Thomas
(74) *Attorney, Agent, or Firm*—Henry Policinski; Joseph S. Heino; Patrick M. Bergin

(57) ABSTRACT

The present invention provides a method to detect tube spits and to reduce spit related artifacts in a computed tomography imaging system. A way of detecting tube spit is to monitor the generator kilovolt or milliamp waveforms. Changes in kV waveform follow closely with those in offset-corrected projection data. If a tube-spit event is not detected, processing proceeds without tube spit correction. If a tube-spit event is detected, a tube spit correction is performed. The objective of tube-spit correction is to remove image artifacts due to the occurrence of a tube-spit event.

23 Claims, 3 Drawing Sheets

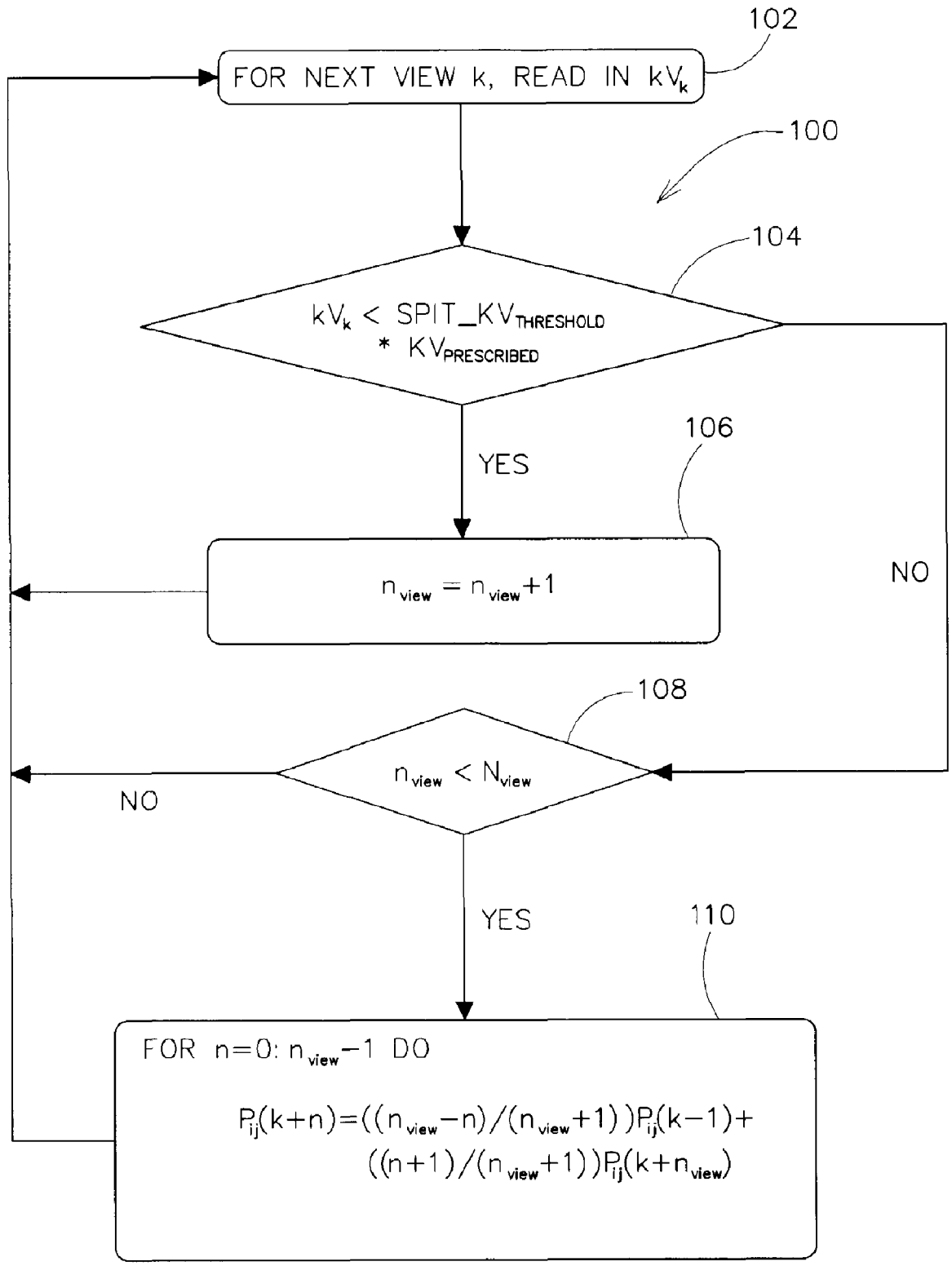

METHOD FOR TUBE SPIT CORRECTION BASED ON HIGH VOLTAGE OUTPUT

BACKGROUND OF INVENTION

This invention relates generally to methods and apparatus for CT imaging and other radiation imaging systems, and more particularly to detecting and correcting data for tube-spit events.

In at least some computed tomography (CT) imaging system configurations, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. X-ray sources typically include x-ray tubes, which emit the x-ray beam at a focal spot. X-ray detectors typically include a collimator for collimating x-ray beams received at the detector, a scintillator adjacent the collimator, and photodetectors adjacent the scintillator.

The term "tube-spit" refers to temporary electrical short-circuit that sometimes occurs inside an x-ray tube. Typically, upon the occurrence of tube-spit, the supply of power to the x-ray tube is temporarily interrupted to prevent arcing. Power is restored to the tube after a time interval of, for example, about one millisecond. During tube-spit recovery, no x-ray photon is emitted from the x-ray tube. As a result, detector measurements taken during the recovery are invalid.

Generally, tube-spit recovery time should be shorter than the data acquisition sampling interval to avoid image artifacts. As data sampling rates increase, a recovery time of about one millisecond is too long to avoid artifact generation.

SUMMARY OF INVENTION

What is needed is a method for tube-spit detection and correction that can be performed utilizing software processing rather than increasing demands on hardware by reducing the time interval between switching power to the x-ray tube off and then on again.

The algorithm described in the present method is used to detect tube spits and to reduce spit related artifacts. Detection of tube spit is the first and most important step of the algorithm. When tube spits, both voltage and current from the generator drop significantly, if not to zero. Therefore, one way of detecting tube spit is to monitor the generator kilovolt or milliamp waveforms. When plotted, kV waveform and related projection view data collected from a CT system with a spitting tube show that changes in kV waveform at a spit location follow closely with those in offset-corrected projection data. Therefore, generator kV waveforms can be used to detect views corrupted by tube spits.

If a tube-spit event is not detected, processing proceeds without tube spit correction. If a tube-spit event is detected, a tube spit correction is performed. In addition, if a tube-spit event is detected, power may still be interrupted to the x-ray tube. The tube-spit correction described herein, however, eliminates a need to increase demands on hardware by reducing the time interval between interrupting power to the x-ray tube as compared to the time interval described above. That is, even with increased sampling rates, the time interval for interrupting power to the x-ray tube need not be reduced. Generally, the objective of tube-spit correction is to remove image artifacts due to the occurrence of a tube-spit event.

BRIEF DESCRIPTION OF DRAWINGS

FIG. 4 is a flow chart illustrating tube-spit detection and correction processing.

DETAILED DESCRIPTION

Figure 1:
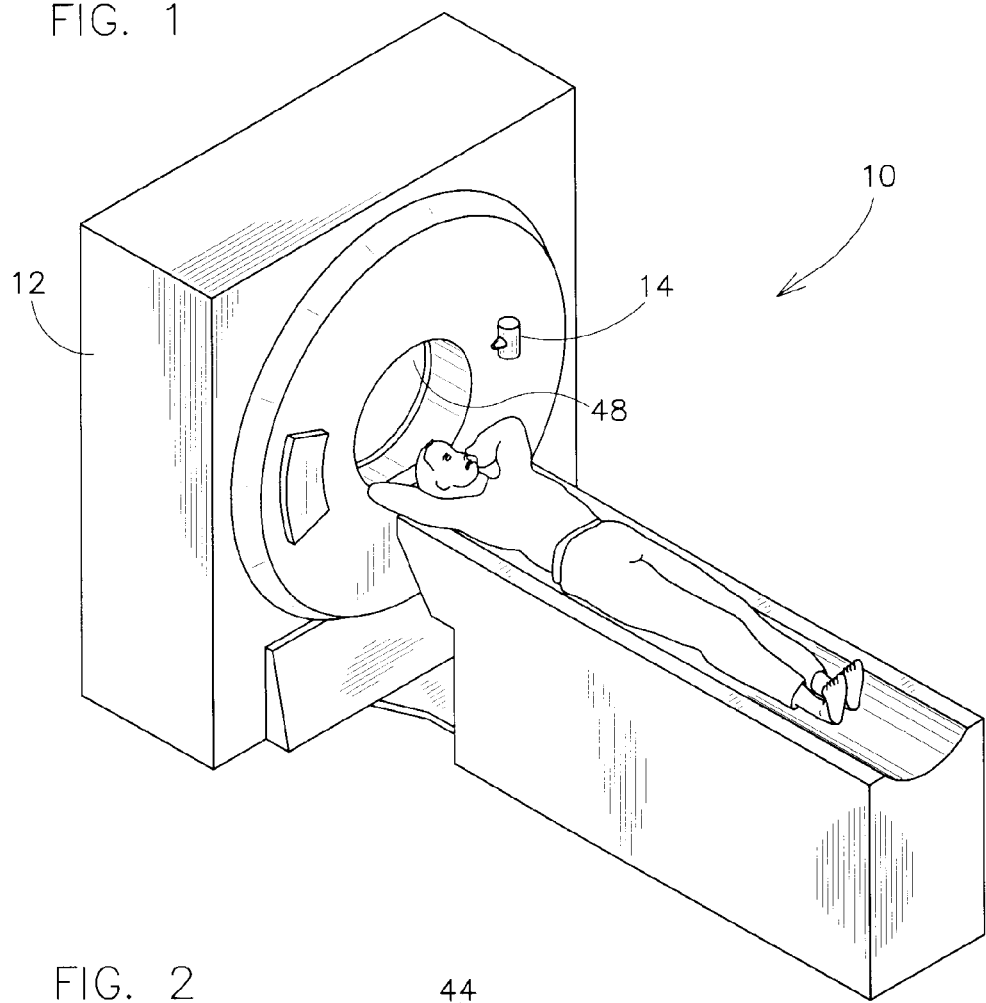
FIG. 1 is a pictorial view of a CT imaging system.
Figure 2:
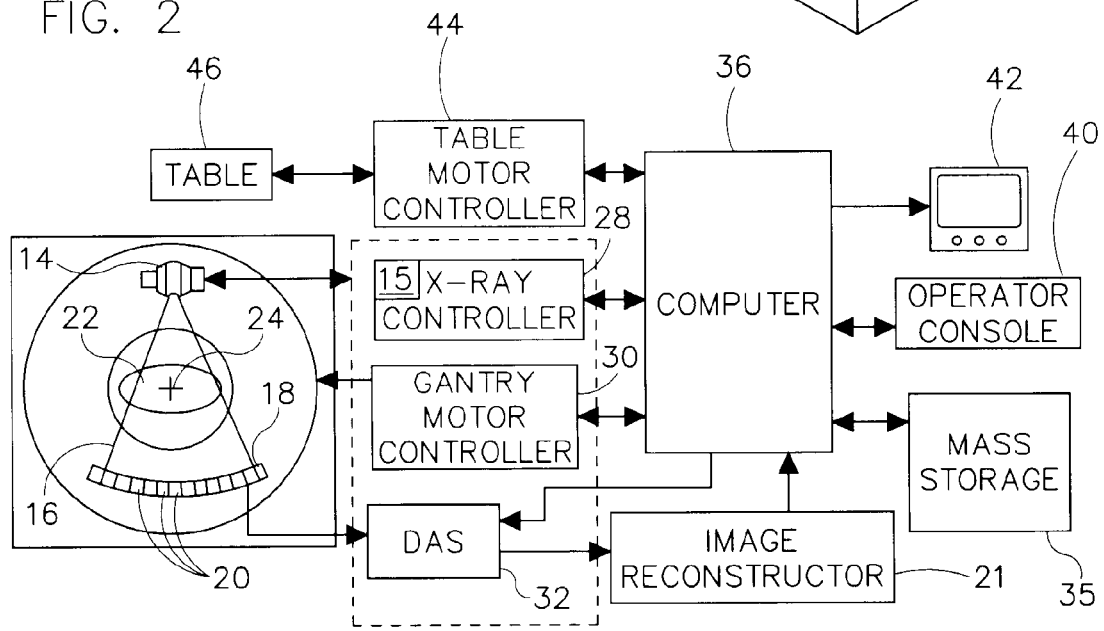
FIG. 2 is a block schematic diagram of the system illustrated in FIG. 1.

Referring now to the drawings in detail, wherein like numbered elements refer to like elements throughout, FIGS. 1 and 2 refer to a computed tomography (CT) imaging system 10. The CT imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through an object, such as a medical patient 22. Each detector element 20 produces an electrical signal that represents the intensity of an impinging x-ray beam and hence the attenuation of the beam as it passes through an object or a patient 22. During a scan to acquire x-ray projection data, gantry 12 and the components mounted thereon rotate about a center of rotation 24. In one embodiment, and as shown in FIG. 2, detector elements 20 are arranged in one row so that projection data corresponding to a single image slice is acquired during a scan. In another embodiment, detector elements 20 are arranged in a plurality of parallel rows, so that projection data corresponding to a plurality of parallel slices can be acquired simultaneously during a scan.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

X-ray source 14 includes an x-ray generator 15 for providing power to x-ray tubes. The x-ray generator 15 converts electrical power from a commercial AC power source to high-voltage DC at a selected voltage and for a suggested duration as instructed by the x-ray controller 28. The x-ray generator 15 preferably also regulates the power supply to the x-ray tubes. The x-ray controller 28 may be separate or integrated with a universal control system.

FIG. 4 is a flow chart depicting a method for tube spit detection and correction processing 100 in accordance with one embodiment of the present invention. Detection and correction of the tube spits is performed by a processor in DAS 32, image reconstructor 24, or computer. Rather than increasing the demands on hardware by reducing the timer interval between interrupting power to the x-ray tube and then re-energizing the tube during a recovery period, the detection and correction processing in FIG. 4 is performed utilizing software control processing. Therefore, the difficulties associated with hardware and speed limitations as described above are substantially, if not entirely, avoided and not dependent on the sampling rate of DAS 32.

Reference is now made specifically to FIG. 4, which provides in detail the method for tube spit monitoring 100 disclosed by the present invention. In brief, the projection data is continuously monitored 102. Each kilovolt value $kV_k$ is then compared to a threshold value ($kV_{spit\ threshold}$) 104 multiplied by a prescribed kV ($kV_{prescribed}$). If the value is above the threshold, the computer automatically processes the next value 106. If, however, the measured value is below the threshold, the view may be corrupted and the computer moves on to a preliminary processing stage 108. The only activity at this stage is to determine how many of the immediately preceding views have been corrupted. If the number of corrupted views is less than the maximum allowable number of corrupted views, $N_{view}$, a view interpolation is performed 110. While there are many methods for tube spit detection, one such method is described below in much more detail.

Figure 3A:
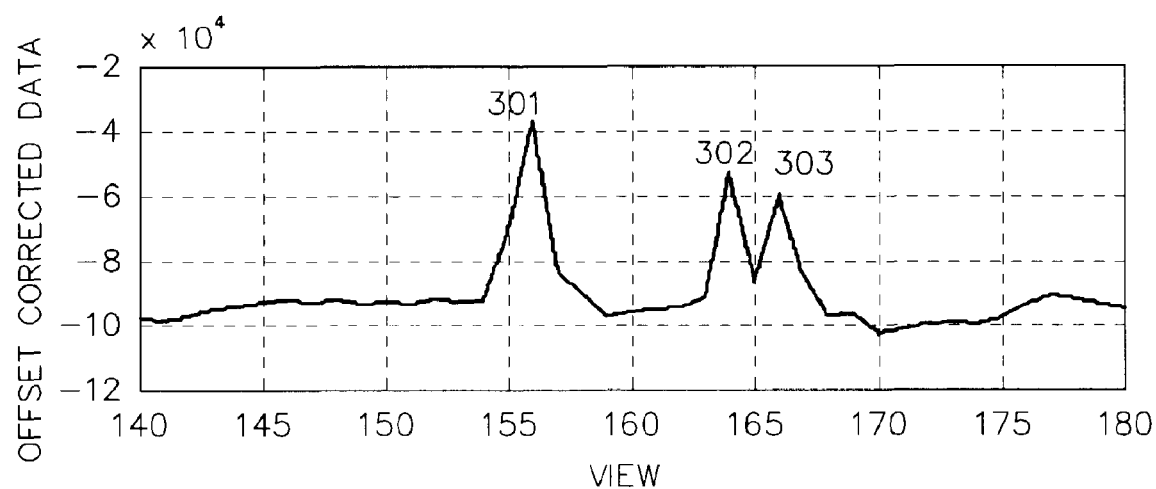
FIG. 3 is a set of kV waveform and related offset-corrected projection data collected from a CT system experiencing a tube spit.
Figure 3B:
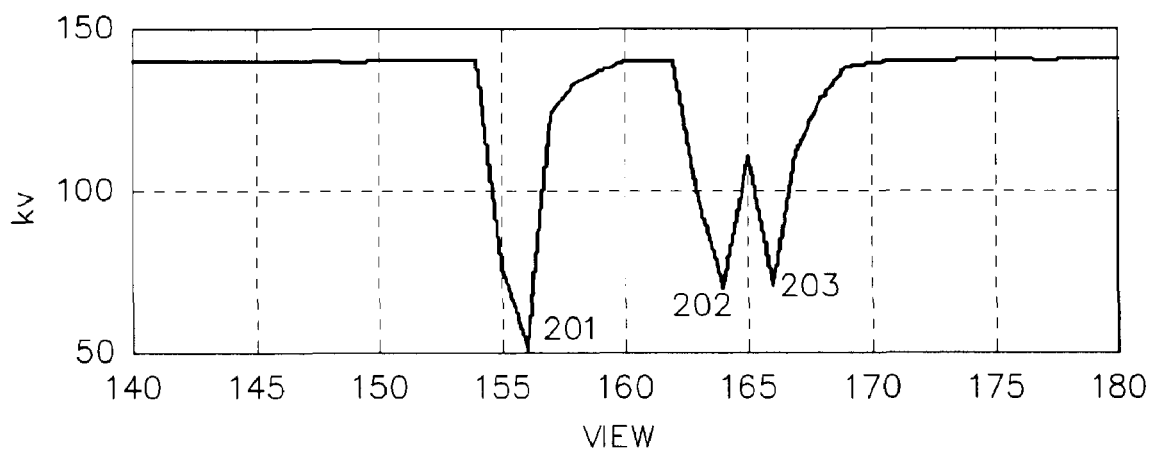

The general objective of tube spit detection 104 is to determine whether the x-ray source experiences a drop in power. FIG. 3A and FIG. 3B, show a graph of the generator output in kilovolts and the related projection data for an x-ray experiencing a tube spit event. In particular, where the generator output drops, as indicated by reference numeral 201, 202 and 203, the projection data, as shown in FIG. 3A is corrupted. The corrupted data 301, 302 and 303 correspond to the generator output drops. Therefore, unlike earlier methods, the present method monitors the generator waveform directly. If the generator output drops to a threshold value, a tube spit event is declared. For example, the operator could decide that for a particular scan, it is important that very little data is corrupted, therefore, the kV threshold may be set at 125 kV. After tube spit detection 104, tube spit correction is performed 110, the image is processed further, and the image is reconstructed.

First, two parameters have to be set in order for the program to perform properly. The first value is the threshold value, $kV_{threshold}$, for the generator voltage $kV_{prescribed}$. The present method calls for entry of that voltage as a fraction of the nominal voltage. Whenever the generator voltage dips below the specified fraction of the nominal voltage, the method for tube spit correction is initiated. Obviously, this value should be optimized to maximize the spit correction rate. The second value required is the maximum allowable number of corrupted views $N_{view}$. Obviously, as the maximum allowable number of corrupted images rises, the quality of the image decreases. (However, in general, these two parameters are set by the manufacturer of the CT scanner.) The monitoring block 102 simply receives information as to the value of the generator voltage $kV_k$. The monitoring block 102 then reports the value to the detection block 104. The detection block compares $kV_k$ to $kV_{threshold}*kV_{prescribed}$. $kV_{prescribed}$ is a value set by the user during scan protocol prescription. $kV_{threshold}$ is also a fractional value determined previously. Following detection of the tube spit criteria, a counter is initiated 106. If the counter exceeds the maximum number of allowable corrupted images $N_{view}$, a warning message is posted to the operator, and service personnel would be contacted for a possible tube change.

If, however, a momentary tube spit occurred, and the number of unacceptable $n_{view}$ views is under the threshold 108, new views will be generated in place of the corrupted views using linear or high-order interpolation between the adjacent non-corrupted views 110. Other methods for interpolation, which are well known in the art could also be used. The preferred interpolation method is shown below.

$$P_{ij}(k+n)=((n_{view}-n)/(n_{view}+1))P_{ij}(k-1)+((n+1)/(n_{view}-1))P_{ij}(k+n_{view})$$

Note that $P_{ij}(k+n)$ is the projection at channel i, detector row j, view number k+n. k is the view number right before the tube spit.

There are many possible methods for monitoring tube spit. For example, the most basic method would be to provide a voltmeter or ammeter to measure the voltage output to the x-ray source. The voltmeter would then be electronically connected to the computer which would initiate the tube spit correction method in the event a tube spit occurred.

Another possible method would be to use the x-ray controller 28 to monitor the voltage directly. The x-ray controller 28 is electronically connected to the computer 36 such that, in the event that a voltage decrease is detected by the x-ray controller, a tube spit event is declared by the computer 36 and the method for tube spit correction begins.

Yet another example would provide a voltage or current measuring device connected in an electronic manner to the DAS 32 or computer 36, which would initiate the method for tube spit correction. There are many devices for measuring electrical current and/or voltage and many devices capable of communicating the voltage and/or current measurement to a processor or computer and several have been described above. The inventors do not intend for the devices used to measure the voltage and/or current or the devices that communicate the voltage and/or current to be limitations of the present invention.

Yet another example is to store the history of the tube spit occurrence. If the frequency or the magnitude of the tube spit exceed certain threshold, operator and service engineers will be notified for tube replacement. Note that frequent tube spit is an indication of "end-of-life" for the tube. This feature allows the replacement of the tube before its complete failure to reduce the down time of the system.

In summary, the method of the present invention provides for a method comprising the steps of: providing an x-ray controller for monitoring the output of a CT system generator; providing a computer to monitor the generator output from a CT system generator; setting a voltage threshold that, if the voltage to the x-ray controller falls below, a tube-spit event is declared; determining the number of corrupted views; warning the operator if the maximum number of corrupted views has been exceeded; and if a tube spit occurred, performing tube spit correction. The method also provides a warning to the operator that the maximum allowable number of corrupted views has been exceeded. The method of the present invention further provides for using some form of view interpolation, whether it is linear, high-order or follows the form:

$$P_{ij}(k+n)=((n_{view}-n)/(n_{view}+1))P_{ij}(k-1)+((n+1)/(n_{view}+1))P_{ij}(k+n_{view})$$

wherein $P_{ij}(k+n)$ is the projection at channel i, detector row j, view number k+n. The method of the present invention further comprises the step of storing the history and magnitude of tube spit occurrences and notifying the operator and/or service personnel of the need to change the x-ray tube.

The method of the present invention uses kV generator waveforms to detect tube spit. Compared with prior methods this new method is easier to implement and faster because it doesn't require projection data processing to determine if tube spit occurred. Prior devices used projection data to detect tube spit, which is much more computation intensive and difficult to implement.

Although the inventors have very specifically described the preferred embodiments of the invention herein, it is to be understood that changes can be made to the improvements disclosed without departing from the scope of the invention. Therefore, it is to be understood that the scope of the invention is not to be overly limited by the specification and the drawings, but is to be determined by the broadest possible interpretation of the claims.

The invention claimed is:

1. A method for detecting and correcting tube spit comprising the steps of:
   providing a CT system generator having a generator output voltage
   providing a computer, the computer being in electronic communication with the generator and being capable of detecting fluctuations in generator output voltage;
   monitoring the generator output voltage;
   detecting any drops in generator output voltage;
   determining whether a tube-spit event occurred; and
   if a tube spit occurred, performing tube spit correction.

2. The method of claim 1 wherein the generator generates kV or mA waveforms and wherein the step of determining whether a tube spit event has occurred includes the step of monitoring either the generator kV or mA waveforms.

3. The method of claim 2 wherein the step of determining whether a tube spit event occurred further comprises determining whether generator output dropped below a threshold value.

4. The method of claim 2 further comprising the step of setting a generator output threshold, wherein if the generator output falls below the threshold, a tube spit event is declared.

5. The method of claim 4 further comprising the step of determining a number of corrupted views that need to be corrected.

6. The method of claim 5 further comprising the step of providing a warning to an operator if the number of corrupted views exceeds a maximum allowable number of corrupted views.

7. The method of claim 6 further comprising the step of storing a history and magnitude of tube spit occurrences.

8. The method of claim 7 further comprising the step of notifying the operator and/or service personnel of a need to change the x-ray tube.

9. The method of claim 8 further comprising the step of using view interpolation between two most recent good images to replace the corrupted views in between.

10. The method of claim 9 wherein the view interpolation is performed in accordance with:

$$P_{ij}(k+n)=((n_{view}-n)/(n_{view}+1))P_{ij}(k-1)+((n+1)/(n_{view}+1))P_{ij}(k+n_{view})$$

wherein $P_{ij}(k+n)$ is the projection at channel i, detector row j, view number k+n.

11. A processor programmed to:
   monitor the generator output from a CT system generator;
   monitor the generator output voltage;
   detect any drops in generator output voltage
   determine whether a tube-spit event occurred; and
   if a tube spit occurred, perform tube spit correction.

12. The method of claim 11 wherein the generator generates kV or mA waveforms and wherein the step of determining whether a tube spit event has occurred includes the step of monitoring either the generator kV or mA waveforms.

13. The method of claim 12 further comprising the step of determining a number of corrupted views that need to be corrected.

14. The method of claim 13 further comprising the step of providing a warning to an operator if the number of corrupted views exceeds a maximum allowable number of corrupted views.

15. The method of claim 14 further comprising the step of storing a history and magnitude of tube spit occurrences.

16. The method of claim 14 further comprising the step of notifying the operator and/or service personnel of a need to change the x-ray tube.

17. The method of claim 15 further comprising the step of using view interpolation between two most recent good images to replace the corrupted views in between.

18. The method of claim 16 wherein the view interpolation is performed in accordance with:

$$P_{ij}(k+n)=((n_{view}-n)/(n_{view}+1))P_{ij}(k-1)+((n+1)/(n_{view}+1))P_{ij}(k+n_{view})$$

wherein $P_{ij}(k+n)$ is the projection at channel i, detector row j, view number k+n.

19. A method for detecting and correcting tube spit in a CT system comprising the steps of:
   providing an x-ray controller for monitoring the output of a CT system generator;
   providing a computer to monitor the generator output from a CT system generator, the computer being in electronic communication with the x-ray controller and the CT system generator;
   setting a voltage threshold that, if the computer determines that the voltage to the x-ray controller is below the threshold, a tube-spit event is declared;
   determining a number of corrupted views;
   warning an operator if a maximum number of corrupted views has been exceeded; and
   if a tube spit occurred, performing tube spit correction.

20. The method of claim 19 further comprising the step of storing a history and magnitude of tube spit occurrences.

21. The method of claim 20 further comprising the step of notifying the operator and/or service personnel of a need to change the x-ray tube.

22. The method of claim 21 further comprising the step of using view interpolation between a two most recent good views to replace the corrupted views in between 110.

23. The method of claim 22 wherein the view interpolation is performed in accordance with:

$$P_{ij}(k+n)=((n_{view}-n)/(n_{view}+1))P_{ij}(k-1)+((n+1)/(n_{view}+1))P_{ij}(k+n_{view})$$

wherein $P_{ij}(k+n)$ is the projection at channel i, detector row j, view number k+n.

* * * * *